United States Patent
Zhang (10) Patent No.: US 9,322,103 B2
(45) Date of Patent: Apr. 26, 2016

(54) BIOSENSOR MEMBRANE COMPOSITION, BIOSENSOR, AND METHODS FOR MAKING SAME

(75) Inventor: Yanan Zhang, Waltham, MA (US)

(73) Assignee: Microchips Biotech, Inc., Lexington, MA (US)

( * ) Notice: Subject to any disclaimer, the term of this patent is extended or adjusted under 35 U.S.C. 154(b) by 325 days.

(21) Appl. No.: 13/813,889

(22) PCT Filed: Aug. 5, 2011

(86) PCT No.: PCT/US2011/046714
§ 371 (c)(1),
(2), (4) Date: Feb. 1, 2013

(87) PCT Pub. No.: WO2012/019083
PCT Pub. Date: Feb. 9, 2012

(65) Prior Publication Data
US 2013/0126349 A1    May 23, 2013

Related U.S. Application Data (60) Provisional application No. 61/371,331, filed on Aug. 6, 2010.

(51) Int. Cl.
*B01D 39/00* (2006.01)
*B01D 39/14* (2006.01)
(Continued)

(52) U.S. Cl.
CPC ............ *C25B 13/08* (2013.01); *B01D 67/0088* (2013.01); *B01D 69/144* (2013.01);
(Continued)

(58) Field of Classification Search
CPC .... B01D 71/54; B01D 71/70; B01D 2323/12; B25B 13/08; C12Q 1/002; C25B 13/08; A61B 5/14865

USPC ............................................ 210/500.27, 490
See application file for complete search history.

(56) References Cited

U.S. PATENT DOCUMENTS

| 4,828,705 A | 5/1989 | Thakore et al. |
| 4,968,532 A | 11/1990 | Janssen et al. |

(Continued)

FOREIGN PATENT DOCUMENTS

| WO | 01/32303 A1 | 5/2001 |
| WO | 2006/018425 A2 | 2/2006 |

(Continued)

OTHER PUBLICATIONS

PCT International Search Report for PCT Application No. PCT/US2011/046714 mailed Feb. 14, 2012 (3 pages).

(Continued)

*Primary Examiner* — Ana Fortuna
(74) *Attorney, Agent, or Firm* — Sutherland Asbill & Brennan LLP (57) ABSTRACT

Selectively permeable membranes for biosensors are provided. In one embodiment, the membrane includes a polymer mixture that includes a polyurethane component, a siloxane component, and a hydrogel component, the components in the mixture in amounts of about 60 to about 80 wt % polyurethane, about 10 to about 20 wt % siloxane, and about 10 to about 20 wt % hydrogel. The membrane has a surface restructured to be hydrophilic, with the restructured surface being crosslinked ed via reactive end groups on at least one of the polyurethane, the siloxane, and the hydrogel components. In another embodiment, the membrane includes a solvent cast film which includes a mixture of a first polyether-based thermoplastic polyurethane copolymer, a polyether-based polyurethane copolymer, and, optionally, a second polyether-based thermoplastic polyurethane copolymer.

14 Claims, 2 Drawing Sheets

(51) Int. Cl.
*B29C 65/00* (2006.01)
*B29C 41/00* (2006.01)
*C25B 13/08* (2006.01)
*C12Q 1/00* (2006.01)
*B01D 67/00* (2006.01)
*B01D 71/54* (2006.01)
*B01D 71/70* (2006.01)
*B01D 69/14* (2006.01)
*A61B 5/1486* (2006.01)
*G01N 27/327* (2006.01)

(52) U.S. Cl.
CPC ............... *B01D 71/54* (2013.01); *B01D 71/70* (2013.01); *C12Q 1/002* (2013.01); *A61B 5/14865* (2013.01); *B01D 2323/12* (2013.01); *B01D 2323/16* (2013.01); *B01D 2323/30* (2013.01); *B01D 2325/36* (2013.01); *G01N 27/3271* (2013.01)

(56) References Cited

U.S. PATENT DOCUMENTS

| | | | |
|---|---|---|---|
| 5,428,123 A | 6/1995 | Ward et al. | |
| 5,700,286 A * | 12/1997 | Tartaglia et al. | 623/1.15 |
| 5,897,955 A | 4/1999 | Drumheller | |
| 6,123,861 A | 9/2000 | Santini, Jr. et al. | |
| 6,284,137 B1 | 9/2001 | Hajikano et al. | |
| 6,379,381 B1 * | 4/2002 | Hossainy et al. | 623/1.42 |
| 6,551,838 B2 | 4/2003 | Santini, Jr. et al. | |
| 7,157,528 B2 | 1/2007 | Ward | |
| 7,226,978 B2 | 6/2007 | Tapsak et al. | |
| 7,445,712 B2 | 11/2008 | Herron | |
| 7,510,551 B2 | 3/2009 | Uhland et al. | |
| 7,537,590 B2 | 5/2009 | Santini, Jr. et al. | |
| 7,858,110 B2 * | 12/2010 | Kuzma et al. | 424/423 |
| 8,095,197 B2 | 1/2012 | Santini, Jr. et al. | |
| 8,414,489 B2 | 4/2013 | Shah et al. | |
| 9,078,900 B2 * | 7/2015 | Kuzma et al. | |
| 2004/0033251 A1 * | 2/2004 | Sparer et al. | 424/425 |
| 2005/0112650 A1 * | 5/2005 | Chang et al. | 435/6 |
| 2006/0258761 A1 | 11/2006 | Boock et al. | |
| 2007/0135698 A1 | 6/2007 | Shah et al. | |
| 2007/0244379 A1 | 10/2007 | Boock et al. | |
| 2007/0276477 A1 * | 11/2007 | Lee et al. | 623/1.44 |
| 2008/0033269 A1 | 2/2008 | Zhang | |
| 2010/0147763 A1 | 6/2010 | Tsou et al. | |
| 2010/0252428 A1 | 10/2010 | Lauks et al. | |

FOREIGN PATENT DOCUMENTS

| | | |
|---|---|---|
| WO | 2006/062668 A2 | 6/2006 |
| WO | 2007/120129 A1 | 10/2007 |
| WO | 2011/084651 A1 | 7/2011 |

OTHER PUBLICATIONS

Berrocal et al., "Reducing the Thrombogenicity of Ion-Selective Electrode Membranes Through the Use of a Silicone-Modified Segmented Polyurethane," Anal. Chem., 2001, 73:5328-5333.

Bindra et al., "Design and in Vitro Studies of a Needle-Type Glucose Sensor for Subcutaneous Monitoring," Anal. Chem. 1991, 63:1692-1696.

Yu et al., "A Long-Term Flexible Minimally-Invasive Implantable Glucose Biosensor Based on an Epoxy-Enhanced Polyurethane Membrane," Biosensors and Bioelectronics, 2006, 21:2275-2282.

Tecophilip SP-80A-150—Lubrizol—Thermoplastic Polyurethane Elastomer (Polyether), http://www.ides.com/grades/ds/E102085.htm, 2010.

PurSil AL—Aliphatic Thermoplastic Silicone Polyether Urethane, 2006, 2 pages.

Supplementary European Search Report for EP Application No. 11 81 5362 mailed Jul. 16, 2014 (8 pages).

* cited by examiner

BIOSENSOR MEMBRANE COMPOSITION, BIOSENSOR, AND METHODS FOR MAKING SAME

CROSS-REFERENCE TO RELATED APPLICATION

This application is a national phase entry of PCT Patent Application No. PCT/US2011/046714, filed on Aug. 5, 2011, designating the United States of America, and claims the benefit of U.S. Provisional Patent Application No. 61/371,331, filed on Aug. 6, 2010, which is incorporated herein by reference.

FIELD OF INVENTION

The present invention relates generally to biosensors and associated membranes, which may be used in the detection of analytes in humans or animals.

BACKGROUND

Chemical and electrochemical biosensors are useful in medicine and chemistry for determining the presence or concentration of analytes. Typically, some biosensors produce signals which are related to the concentration of an analyte. Biosensors are important medical tools because of their ability to measure the concentrations of molecules which are indicative of various conditions, diseases, or disorders, and therefore a patient's need for treatment.

Biosensors may be exemplified by devices which comprise an enzyme layer and utilize electrodes. The electrodes are able to detect chemical species such as oxygen. When enzyme layers attached to the electrodes catalyze a reaction, a chemical is produced. This chemical is detected by a specific electrode. Therefore, it is often important to limit the analytes that may come into contact with the enzyme layer of a biosensor. This task may be achieved by a selectively permeable membrane.

A need exists, however, for better selectively permeable membranes and methods of production. Known conventional membrane materials typically have insufficient adhesion to substrates, poor blocking efficiency to interfering species and/or unsatisfactory dimensional stability. For long term sensors, in particular, instability of the membrane results in more signal drift which necessarily requires more frequent calibration and may cause a reduction in sensor lifetime. It therefore would be desirable to provide membrane materials that reduce or some or all of these deficiencies, particularly for implantable biosensors intended for use over an extended period. In addition, there is a need for such a selectively permeable membrane to be reproducibly manufacturable.

SUMMARY

In one aspect, a selectively permeable membrane for a biosensor is provided. The membrane may comprise a polymer mixture which comprises a poly urethane component a siloxane component, and a hydrogel component. In certain embodiments, these components are present in the mixture in amounts of about 60 to about 80 wt % polyurethane, about 10 to about 20 wt % siloxane, and about 10 to about 20 wt % hydrogel. The membrane also may have a surface which is restructured to be more hydrophilic. The polymer mixture with the restructured surface may also be crosslinked via reactive end groups on at least one of the polyurethane component, the siloxane component, or the hydrogel component.

Biosensors comprising these or similar membranes are also provided. For example, the biosensor may include a substrate, at least one electrode disposed on the substrate, at least one enzyme layer disposed on the at least one electrode, and at least one selectively permeable membrane fixed on the at least one enzyme layer.

In another aspect, a method is provided for making a selectively permeable membrane. In one embodiment, the method includes the following steps: mixing a polyurethane component, a siloxane component, and a hydrogel component together with a first solvent for the components to form a polymer solution mixture; depositing the polymer solution mixture on a substrate evaporating the first solvent from the polymer solution mixture to form a film of a polymer mixture, the film having a surface opposing the substrate; applying a solvent mixture onto the surface of the film to partially re-dissolve and swell the film, wherein the solvent mixture comprises a hydrophilic constituent and a hydrophobic constituent; and evaporating the sol vent mixture from the partially redissolved and swollen film to reform the surface with hydrophilic molecules of the polymer mixture redistributed toward the reformed surface.

In still another aspect, a selectively permeable membrane that comprises a solvent cast film is provided for a biosensor. In certain embodiments, the film comprises a first polyether-based thermoplastic polyurethane copolymer, and a polyether-based polyurethane copolymer, wherein the polyether-based thermoplastic polyurethane copolymer, or the poly ether-based polyurethane copolymer, or both comprise at least one siloxane repeat unit. In certain embodiments, the film comprises a second polyether-based thermoplastic polyurethane copolymer, which may comprise at least one siloxane repeat unit.

In yet another aspect, a casting method is provided for making a selectively permeable membrane. In one embodiment, the method includes: applying onto a substrate a polymer solution mixture which comprises a first polyether-based thermoplastic polyurethane copolymer and a polyether-based polyurethane copolymer, wherein the polyether-based thermoplastic polyurethane copolymer, or the polyether-based polyurethane copolymer, or both comprise at least one siloxane repeat unit, in solution with a volatile organic solvent; and evaporating the volatile organic solvent from the polymer solution mixture to form a film of a polymer mixture on the substrate. In certain embodiments, the polymer solution mixture further comprises a second polyether-based thermoplastic polyurethane copolymer, which may comprise at least one siloxane repeat unit.

DETAILED DESCRIPTION

The membranes described herein generally comprise a polymer mixture. In certain embodiments, the polymer mixture comprises a polyurethane component, a siloxane component, and a hydrogel component. These component are present in the polymer mixture in amounts of about 60 to about 80 percent by weight polyurethane, about 10 to about 20 percent by weight siloxane, and about 10 to about 20 percent by weight hydrogel. The weight percentages are calculated based on the total weight of the polymer mixture. In a particular embodiment, the components are present in the polymer mixture in amounts of about 75 percent by weight polyurethane, about 15 percent by weight silicone, and about 10 percent by weight hydrogel. The polymeric mixture may be homogeneous or heterogeneous.

The Polyurethane Component

Generally, the polyurethane component comprises a polymer with substantially organic units joined by urethane-type linkages (N—(CO)—O). Polymers with urethane-type linkages commonly are formed by the reaction of difunctional isocyanates with difunctional alcohols. The polyurethane component of the present disclosure may also contain some urea-type linkages (N—(CO)—N). Polymers with urea-type linkages commonly are formed by the reaction of difunctional isocyanates with difunctional amines. The polyurethane component described herein may be a polymer with both urethane-type and urea-type linkages.

Therefore, the polyurethane component described herein may be a copolymer, block copolymer, or segmented copolymer having the following structure:

wherein m, and n independently equal 0 to 1000; and, in each instance, R, R', R", and R''' are independently selected from a divalent $C_1$-$C_{20}$ hydrocarbyl.

A $C_1$-$C_{20}$ hydrocarbyl may be selected from an aliphatic group, an aromatic or aryl group, a cyclic group, or any combination thereof, any substituted derivative thereof, including but not limited to any halide-, alkoxide-, or amide-substituted derivative thereof. Also included in the definition of the $C_1$-$C_{20}$ hydrocarbyl are any unsubstituted, branched, or linear analogs thereof. The $C_1$-$C_{20}$ hydrocarbyl may be substituted with one or more functional moieties selected from a halide, an ether, a ketone, an ester, an amide, a nitrile, a heterocycle comprising at least one N-, O-, or S-heteroatom, an aldehyde, a thioether, an imine, a sulfone, a carbonate, a urethane, a urea or an imide.

The polyurethane component may also comprise commercially-available polyurethanes, such as, for example, BIOSPAN®; BIOSPAN®-S, PURSIL® AL (The Polymer Technology Group, Berkeley, Calif., U.S.A.); TECOPHILIC™ SP-85A-150; or TECOFLEX™ SG 85A (Lubrizol Advanced Materials, Cleveland. Ohio, U.S.A.).

The polyurethanes described herein may be formulated to provide good biocompatibility, flexural endurance, high strength, and/or processing versatility over a wide range of applications. The polyurethane component's structure may provide mechanical strength in the membranes described herein. Therefore, the membranes may be stable for long-term applications, particularly in implantable devices.

The Siloxane Component

The siloxane component described herein consists of a polymer comprising at least one siloxane repeat unit. As described herein, a siloxane repeat unit has the following general structure:

wherein p equals 1 to 10,000; and $R^{17}$ and $R^{18}$ are selected independently from hydrogen or a monovalent $C_1$-$C_{20}$ hydrocarbyl as defined herein. It is contemplated that the polymeric structure of the siloxane component may be branched or unbranched.

In particular embodiments, $R^{17}$ and $R^{18}$ are each selected independently from a monovalent $C_1$-$C_{20}$ hydrocarbyl. In these embodiments, two organic side chains are bonded to the silicon atom in the siloxane component. Such a compound is commonly referred to as a silicone.

In particular embodiments, the siloxane component described herein may be selected from polydimethylsiloxane, polydiethylsiloxane, polymethylethylsiloxane, polydipropylsiloxane, polymethylpropylsiloxane, polyethylpropylsiloxane, polydiphenylsiloxane, polypropylphenylsiloxane, polyethylphenylsiloxane, and polymethylphenylsiloxane. Generally, the polydimethylsiloxane adhesive may react or interact with surrounding polymers or substrate surfaces, which may enhance the integrity of the polymer mixture.

The Hydrogel Component

The hydrogel component described herein is generally a water swellable, but water insoluble polymer. The hydrogel component may be selected from a broad class of polymeric materials, which have an affinity for water and typically swell in water, but which do not necessarily dissolve in water. Typically, the hydrogel component is a polymer formed by polymerization and optional cross-linking of a hydrophilic monomer in an aqueous solution.

The hydrogel component described herein may be an organic or inorganic polymer. Organic gels from which the hydrogel component may be selected include, but are not limited to, gels formed from polysaccharides and mucopolysaccharides including, but not limited to hyaluronic acid, dextran, heparin sulfate, chondroitin sulfate, heparin, agar, starch, and alginate; polyaminoacids; proteins that support cell growth and healing, including but not limited to fibronectin, gelatin, collagen, fibrin, pectins, albumin, ovalbumin, and polyamino acids; collagen-hydroxyethyl-methacrylate (HEMA); polyphosphazines; polyphosphoesters; polyethylene glycol, polyethylene glycol which is bis(amine) terminated; polyethylene oxide; polyvinyl alcohol; polyvinylpyrrolidone; polyethyloxazoline; polyethylene oxide-co-polypropyleneoxide block copolymers; PGA-PEG-PGA block copolymers; PGA-PEG diblock copolymers; acrylates, including but not limited to diacrylates, oligoacrylates, methacrylates, dimethacrylates and oligomethoacrylates; PEG-oligoglycolylacrylates, such as described in U.S. Pat. No. 5,626,863, which is incorporated by reference herein in its entirely; carboxy alkyl celluloses, including but not limited to carboxymethyl cellulose; partially oxidized cellulose; biodegradable polymers including but not limited to polymers and oligomers of glycolide, lactide, polylactic acid, polyesters of α-hydroxy acids, including lactic acid and glycolic acid, such as the poly(α-hydroxy) acids including polyglycolic acid, poly-DL-lactic, poly-L-lactic acid, and terpolymers of DL-lactide and glycolide, ε-caprolactone and ε-caprolactone copolymerized with polyesters; polylactones and polycaprolactones including poly(ε-caprolactone), poly(Δ-valerolactone) and poly(γ-butyrolactone); polyanhydrides; polyorthoesters; other hydroxy acids; polydioxanone; and other biologically degradable polymers that are non-toxic or are present as metabolites in the body; as well as non-degradable polymers such as sytrene and acrolein. Each of these polymers may be bis(amine) terminated.

Inorganic gels from which the hydrogel component may be selected include, but are not limited to, silica, alumina, and ferric oxide.

Crosslinking of the hydrogel component may be accomplished by free radical polymerization of hydrophilic monomers, such as hydroxyethyl-methacrylate (HEMA). Hydrogel polymers formed by free radical polymerization of monomer solutions may require crosslinking to form the three dimensional network to gel the aqueous solution. HEMA monomer solutions typically can be crosslinked to gel by dimethacrylate, although other crosslinking agents, such as ethylene glycol dimethacrylate or methylmethacrylate, may also be used during polymerization to modify the hydrogel. A wide variety of other hydrophilic monomers may also be suitable for purposes of this disclosure.

Formation of Membrane

The membranes described herein may be formed by combining the polymers, copolymers, or components described herein. In certain embodiments, the membrane comprises a polyurethane component, a hydrogel component, and a siloxane component, which are combined to form a polymer mixture. The polymer mixture may be mixed with a solvent to form a polymer solution mixture. The solvent may be one that at least partially dissolves the three components of the polymer mixture. In certain embodiments, the solvent is a volatile organic solvent. A volatile organic solvent includes an organic solvent which is readily evaporated at atmospheric pressure or under reduced pressure, preferably without heating. If evaporated under reduced pressure, the solvent may be gently heated. Volatile organic solvents include, but are not limited to, $C_1$-$C_6$ alcohols, acetonitrile, $C_2$-$C_4$ ketones, $C_3$-$C_4$ alkyl esters, $C_2$-$C_6$ ethers, or $C_5$-$C_8$ low-boiling hydrocarbons. In certain embodiments, the volatile organic solvent may be tetrahydrofuran (THF).

In certain embodiments, the solutions of each component may be pre-made and stored until use. Such component solutions may be formulated with the same concentrations so that the measured volume of each solution represents the weight ratio of each component in the resulting mixture.

The polymer solution mixture may be deposited on a substrate or any suitable surface. A number of liquid dispensing methods or techniques may be used to perform the solution deposition. These techniques may allow for the control of the weight, thickness, or basic shape of the deposited polymer mixture solution and, ultimately the film or membrane.

After depositing the polymer mixture solution, the solvent may be allowed to evaporate. As the solvent evaporates from the polymer solution mixture, a film of the polymer mixture may be formed. Generally, the film may have a surface opposing the substrate or other acceptable surface upon which the polymer mixture solution was deposited. This technique is sometimes referred to as solvent casting.

Typically, the films formed by depositing the polymer mixture solution and evaporating the solvent may not be substantially homogeneous, and the surfaces of the films may not have sufficient hydrophilicity. Not wishing to be bound by any particular theory, it is believed that the lack of homogeneity or surface hydrophilicity may be caused by phase segregations among the polymer components, which may be driven by the chemical affinities of the various components. Predicting the permeability of such films may be difficult due to the lack of homogeneity, Not wishing to be bound by any particular theory, it is believed that when organic solvents such as THF evaporate from the films, hydrophobic components may be drawn to the surface of the film. It has been observed that such a film may not be permeable to glucose.

Restructuring the Surface of the Membrane

The surfaces of the membranes described herein may be restructured. Typically, the restructuring increases the hydrophilicity of the film, particularly the hydrophilicity of the surface of the firm. To restructure the surface of the film, a solvent mixture may be applied to at least one surface of the film. The solvent mixture typically comprises a hydrophilic constituent and a hydrophobic constituent. Typically, the solvent mixture does not have the capacity to totally dissolve the film.

Generally, the volume of solvent mixture needed to restructure the film may vary depending on how long it takes a particular solvent mixture to evaporate from the film. Typically, the hydrophilic constituent of the solvent mixture has a lower partial vapor pressure than the hydrophobic constituent. Therefore, the hydrophilic constituent may evaporate from the film more slowly than the hydrophobic constituent. Not wishing to be bound by any particular theory, it is believed that the slower evaporating hydrophilic constituent may cause the more hydrophilic polymer molecules to redistribute toward the surface of the film. Typically, the resulting surface layer may have a higher content of hydrophilic polymer molecules. Generally, such a restructured film or membrane may become more permeable to polar or substantially hydrophilic molecules, such as glucose.

The hydrophobic constituent of the solvent mixture may be an organic solvent, such as a volatile organic solvent as described herein. In certain embodiments, the volatile organic solvent may be THF or a combination of THF and at least one other volatile organic solvent. In certain embodiments, the organic solvent may be toluene or a combination of toluene and at least one other volatile organic solvent. In certain embodiments, the organic solvent may be a combination of THF and toluene. The hydrophilic constituent of the solvent mixture may be any hydrophilic solvent, including water. In certain embodiments, the solvent mixture comprises water and THF. In some of these embodiments, the solvent mixture may comprise water and THF in a volume ratio of about 1:2.

In one embodiment, the solvent mixture is applied on at least one surface of the film. The film may partially re-dissolve and swell upon contacting the solvent mixture. The solvent mixture may then be evaporated from the partially redissolved and swollen film to restructure the surface. As a result, substantially hydrophilic molecules of the polymer mixture may redistribute toward the surface of the film. In certain embodiments, the restructured surface of the film is substantially homogeneous. In certain embodiments, the restructured surface of the film has more hydrophilic character than the surface of the un-restructured film. In certain embodiments, an untreated film that is not permeable to glucose may become permeable to glucose upon restructuring the film's surface with a solvent mixture as described herein.

Typically, the overall shape and mass of the membrane may not be changed by restructuring the surface with the solvent mixture described herein.

Cross-linking the Polymer Mixture

The polymer mixtures described herein may be cross-linked. In certain embodiments, cross-linking may occur via reactive end groups on at least one of the poly urethane component, the siloxane component, or the hydrogel component. At least one component, polymer, or copolymer of the polymer mixtures described herein may be capped with reactive end groups so that the reactive end groups chemically or physically bond or interact with other reactive end groups or at least one cross-linking agent, which may be introduced to the polymer mixture. In certain embodiments, the reactive end groups may chemically react either spontaneously or with available cross-linking reagents under room conditions (i.e. ambient temperature (e.g., 16-27° C.) and atmospheric pressure) or a mild environment. In certain embodiments, the reaction conditions are mild enough that the enzyme layer's function is not impaired Generally, the cross-linked membrane may have good stability and structural integrity.

The reactive end groups may be selected from hydroxy, methacrylate, acrylate, styryl, vinyl benzyl, cinnamate, vinyl, allyl, isopropenyl, benzocyclobutene, benzocyclobutanone, benzocyclobutene dione, epoxy, cyanate, maleimide, amine, ethynyl, trifluorovinyl, amino, methylol, or benzophenone. In certain embodiments, these and other reactive end groups, or combinations thereof may be substituted, preferably at terminal positions, on all of the chemical structures depicted or described herein.

In certain embodiments, a cross-linking agent is introduced to the polymer mixtures described herein. In certain embodiments, the cross-linking agent is introduced as a vapor. In one embodiment, the cross-linking agent is glutaraldehyde.

Methods for capping various polymers with reactive end groups are well-known in the art.

Biosensor

Figure 1:
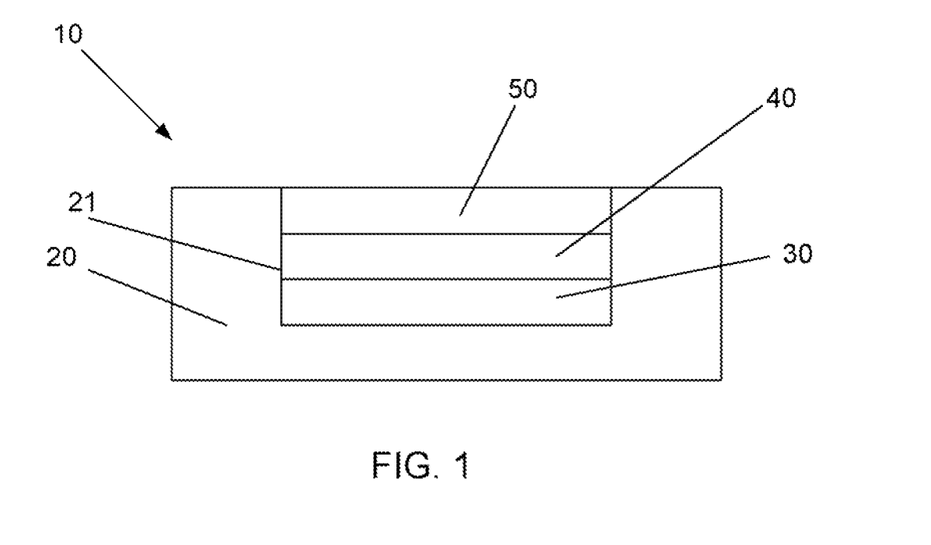
FIG. 1 is a cross-sectional view illustrating a membrane associated with a biosensor.

The membranes described herein may be associated with a biosensor 10, as schematically illustrated in FIG. 1. The biosensor 10 typically comprises a substrate 20, at least one electrode 30 disposed on the substrate 20, at least one enzyme layer 40 disposed on the at least electrode 30, and at least one membrane 50 as described herein disposed on the at least one enzyme layer 40. The substrate 20 may also have a depression 21 or area designed to receive or accommodate the at least one electrode 30, at least one enzyme layer 40, and at least one membrane 50 as described herein. The depression alternatively may be omitted.

The biosensors described herein are suitable for use with external or implantable devices, which contact any biological fluid. That is, the biosensor may be used in an in vitro or in vivo diagnostics device. The biosensors may employ any method of analyte measurement, including enzymatic, chemical, physical, electrochemical, spectrophotometric, polarimetric, calorimetric, radiometric, or other similar techniques.

In certain embodiments, the membranes described herein are used with the amperometric, potentiometric, and conductometric sensor device configurations described in U.S. Patent Application Publication No. 2008/0302659 to Sheppard Jr., et al., which is incorporated herein by reference.

In some embodiments, the biosensors described herein may be associated with an implantable device. Implantable devices may be implanted in soft tissue, such as abdominal, subcutaneous, and periotoneal tissues, the brain, the intramedullary space, and other suitable organs or body tissues. Implanted sensor devices for in vivo monitoring can provide critical information, and can be significantly beneficial to patients in therapy and diagnostics. In one embodiment, the biosensors are disposed at the distal end of a flexible catheter or lead for deployment within a body lumen or other tissue site.

Generally, the biosensors and membranes described herein may be biocompatible, physically and chemically stable, and reproducibly manufacturable. Typically, the membranes describes herein may feature long-term dimensional stability, good adhesion to a substrate, and higher rejection efficiency for electrochemical interferences.

The Substrate

Generally, the substrate may comprise any bio-compatible material. In certain embodiments, the substrate may comprise a variety of materials, including, but not limited to, silicon, glass, metal, quartz, plastic, ceramic, polyethylene, any other suitable polymer, or combinations thereof.

Generally, the substrate may be of any size or shape. In one embodiment, the substrate is planar, as depicted in FIG. 1.

In certain embodiments, the substrate may have a depression or other area designed to receive or accommodate the at least one electrode, at least one enzyme layer, and at least one membrane as described herein. Such a depression or other area may be any suitable shape or size. Typically, the depression or other area on the substrate may be designed with borders which constrain the movement or flow of the polymer solution mixture. In certain embodiments, each electrode on the substrate may be surrounded by an elevated groove. Although the groove may be any size or shape, in some embodiments the elevated groove may form a rectangular closed wall. The walls height may be about 50 micron, in certain embodiments. The wall may be designed to provide a convenient reservoir for liquid dispensing.

The Electrode

The at least one electrode, e.g., the working electrode, of the biosensor described herein may be any suitable material or system for measuring analytes in a biological system. Generally, one or more electrodes may be used in conjunction with the enzyme layer described herein to detect the amount of analyte in a sample and convert the information into a signal. Generally, the electrode oxidizes or reduces an electroactive species. The signal may be transmitted to electronic circuitry required to process any biological information.

U.S. Pat. No. 7,226,978, U.S. Pat. No. 4,757,022, U.S. Pat. No. 5,497,772, and U.S. Pat. No. 4,787,398 describe suitable electronic circuitry, which may be used in the biosensors described herein. Each of these references is incorporated by reference herein. In certain embodiments, the electrode is the working electrode in the amperometric, potentiometric, and conductometric sensor device configurations described in U.S. Patent Application Publication No. 2008/0302659 to Sheppard Jr., et al., which is incorporated herein by reference.

The Enzyme Layer

Generally, the enzyme layer comprises an enzyme which catalyzes a chemical reaction. The chemical reaction may occur between two or more analytes, or between an analyte and another substance (e.g., oxygen) which may or may not be endogenous. In certain embodiments, the enzyme layer may be formed by delivering a volume of an enzyme protein solution to the electrode area of a substrate or other suitable surface. The deposited material may be immobilized with a cross-linker which reacts with the end groups of the protein, particularly those end groups near the surface of the deposited material. In one embodiment, the cross-linker is glutaraldehyde.

In one embodiment, the enzyme layer comprises glucose oxidase. Not wishing to be bound by any particular theory, it is believed that glucose oxidase catalyzes the conversion of oxygen and glucose to hydrogen peroxide and gluconic acid. In other embodiments, the enzyme layer may comprise other oxidases. Other oxidases include, but are not limited to galactose oxidase or uricase.

Membranes Not Requiring Surface Restructuring

In another embodiment, the poly mer mixtures for forming the selectively permeable membrane include a first polyether-based thermoplastic polyurethane copolymer and a polyether-based polyurethane copolymer, wherein the polyether-based thermoplastic polyurethane copolymer, or the polyether-based polyurethane copolymer, or both comprise at least one siloxane repeat unit. The polymer mixture of these components may be used to produce a solvent cast film. In certain embodiments, only the polyether-based polyurethane copolymer comprises at least one siloxane repeat unit. In these embodiments, the proportion of polyether-based thermoplastic polyurethane copolymer to polyether-based polyurethane copolymer comprising at least one siloxane repeat unit is in the range of about 1.3 to about 1:4 by mass.

In yet another embodiment, the membrane comprises a polyether-based thermoplastic polyurethane copolymer a polyether-based polyurethane copolymer, and a second polyether-based thermoplastic polyurethane copolymer. In certain embodiments, each of these three components, independently, may comprise at least one siloxane repeat unit. In certain embodiments, only the polyether-based thermoplastic polyurethane copolymer comprises at least one siloxane repeat unit. In these embodiments, the copolymers are present in the film in a proportion in the range of about 2:1:1 polyether-based polyurethane copolymer to polyether-based thermoplastic polyurethane copolymer to additional polyether-based thermoplastic polyurethane copolymer.

These films also may be associated with a biosensor as described herein. The films may be used instead of or in addition to the films or membranes comprising three polymer components as described hereinabove. Unlike the membranes comprising three components, however, the membranes comprising a first polyether-based thermoplastic polyurethane copolymer, a polyether-based poly urethane copolymer, and, optionally, a second polyether-based thermoplastic polyurethane copolymer, wherein at least one of the components comprises at least one siloxane repeat unit, generally do not require treatment with a solvent mixture to increase the hydrophilicity of the film.

These membranes may also be made by a solvent casting process. The method of solvent casting the membranes is similar to the technique described hereinabove for the membranes comprising three components.

Polyether-Based Thermoplastic Polyurethane Copolymer

The polyether-based thermoplastic and/or the additional polyether-based thermoplastic may be selected independently from any of the polyether-based thermoplastic polyurethane copolymers described herein. In one embodiment, the polyether-based thermoplastic polyurethane copolymer comprises a copolymer which has at least one hydrophobic block and at least one hydrophilic block. Typically, an aliphatic portion is hydrophobic, and the polyurethane portion is hydrophilic. In one embodiment, the polyether-based thermoplastic polyurethane further comprises at least one siloxane repeat unit. In another embodiment, the additional polyether-based thermoplastic polyurethane copolymer further comprises at least one siloxane repeat unit.

In certain embodiments, the polyurethane's hydrophilic block comprises soft segments. These soft segments may comprise polyalkylene oxide units, particularly polyethylene oxide units.

In one embodiment, the polyether-based thermoplastic polyurethane copolymer is TECOPHILIC™ SP-85A-150, which is available from Lubrizol Advanced Materials, Cleveland, Ohio, U.S.A. In another embodiment, the polyether-based polyurethane copolymer is PURSIL® AL (The Polymer Technology Group, Berkeley, Calif., U.S.A.). As described hereinabove, the additional polyether-based thermoplastic polyurethane copolymer also may be selected from these materials.

Polyether-Based Polyurethane Copolymer

The polyether-based polyurethane copolymer generally comprises a copolymer, block copolymer, or segmented copolymer comprising at least one ether-type linkage (R—O—R') and at least one urethane-type linkage (N—(CO)—O). The polyether-based polyurethane copolymer may also comprise at least one urea-type linkage (N—(CO)—N) In certain embodiments, the polyether-based polyurethane copolymer is a copolymer, block copolymer, or segmented copolymer, having the following chemical structure:

wherein a and c independently equal 1 to 10,000, b is equal to 0 to 10,000, and $R^{20}$, $R^{21}$, $R^{22}$, and $R^{23}$ are selected independently from a divalent $C_1$-$C_{20}$ hydrocarbyl, as defined herein.

In certain embodiments, the poly ether-based poly urethane copolymer may comprise at least one siloxane repeat unit. In such embodiments, the polyether-based polyurethane copolymer comprising at least one siloxane repeat unit may have the following chemical structure:

wherein q, r, t, and x independently equal 1 to 10,000; s, u, v, y, and z independently equal 0 to 10,000; $R^1$, $R^2$, $R^3$, $R^{12}$, $R^{13}$, $R^{14}$, $R^{15}$, and $R^{16}$ are independently selected from a hydrogen or a monovalent $C_1$-$C_{20}$ hydrocarbyl, as defined herein; and $R^4$, $R^5$, $R^6$, $R^7$, $R^8$, $R^9$, $R^{10}$, and $R^{11}$ are independently selected from hydrogen or a divalent $C_1$-$C_{20}$ hydrocarbyl, as defined herein.

In one embodiment, the polyether-based polyurethane copolymer comprises a soft segment and a hard segment. In certain embodiments, the soft segment may comprise an aromatic polyetherurethaneurea, the hard segment may comprise polyalkyleneoxide, particularly polytetramethyleneoxide (PTMO). In one embodiment, the polyether-based polyurethane copolymer is BIOSPAN® (The Polymer Technology Group, Berkeley, Calif. U.S.A.). In another embodiment, the polyether-based polyurethane copolymer is a BIOSPAN® polymer comprising at least one silicone repeat unit. This compound is well known in the prior art, and is sometimes referred to as "BIO-SPAN®-S" (Berrocal, M. J et al. Anal. Chem. 2001, 73, 5328-33).

Adjusting the Selective Permeability of the Membranes

The membranes described herein are "selectively permeable." This phrase is used to indicate that the membranes described herein act as a barrier to at least one material, while remaining permeable to at least one other material, possibly an analyte. In some embodiments, the membranes may be permeable to two analytes. In some embodiments, the membrane may be permeable to at least two analytes, and each individual analyte may traverse the membrane at a different rate. In some embodiments, the membrane regulates the flux of various molecules in order to maintain a steady state diffusion of all the molecules involved in the chemical reactions analyzed by a particular device. Generally, due to their selective permeability, the membranes described herein may cover the surface of an enzyme layer or electrode, and control the diffusion of analytes between the enzyme layer or electrode and the surrounding environment. Generally, the membranes may block or minimize unwanted interfering species, which may cause erroneous or non-specific signals.

For instance, acetaminophen is known in the prior art to be a high level interferent to electrochemical sensors. Acetaminophen may be directly oxidized at the electrode, which is polarized above 0.5 V (v. Ag/AgCl) for hydrogen peroxide detection. The level of interference may cause significant bias to sensor signals. The membranes described herein may be highly effective at screening acetominophen from the enzyme layer and electrode.

The selective permeability of the membranes disclosed herein may be controlled and adjusted, in order to tailor a membrane for use in a particular biosensing application. In certain embodiments, the selective permeability of the membranes is adjusted by altering the ratio of the constituents of the membranes. In certain embodiments, the selective permeability of the membranes may be adjusted by altering the ratio of the solvents in the solvent mixture used to restructure the surfaces of the membranes. In one example, the membranes' selective permeability to glucose may be adjusted or controlled. Typically, the selective permeability may be adjusted without reformulating the various polymer mixtures.

Not wishing to be bound by any particular theory, it is generally recognized that the siloxane component is permeable to oxygen. Therefore, increasing the percentage of the siloxane component in three-component membranes described herein may increase the oxygen permeability of the three-component membranes. Similarly, the use of polymers with a greater number of siloxane repeat units in the membranes which do not require surface restructuring may increase the oxygen permeability of the membranes.

Not wishing to be bound by any particular theory, it is generally recognized that the hydrogel component is permeable to glucose. Therefore, increasing the percentage of the hydrogel component in the three-component membranes described herein may increase the glucose permeability of the three-component membranes. In one embodiment, the hydrogel component is polyethylene glycol (PEG). Not wishing to be bound by any particular theory, it is believed that PEG is a good material for ionic transport. This characteristic may be important because it may prevent charges from accumulating inside the membranes. Such an accumulated charge may cause a shift in the applied potential, and increase the overall electrical impedance.

Similarly, increasing the hydrophilic character of the polymers selected for the membranes which do not require surface restructuring may increase their glucose permeability.

Generally, the selective permeability of the membranes may be adjusted by any of the techniques described herein while maintaining other functional parameters. Unlike a typical conventional device, the selective permeability of the membranes described herein may be adjusted without altering the thickness of the membrane. Generally, altering the thickness of a membrane may result in deviations in sensitivity and/or change other intrinsic parameters, such as response time. Typically, since the selective permeability of the membranes described herein may be adjusted without altering the physical and functional parameters, the membranes disclosed herein may be manufactured in a reliably reproducible manner.

Glucose Biosensor

In particular embodiments, the biosensors and membranes described herein may be used as glucose sensors. Typically, a glucose sensor includes a glucose oxidase enzyme which catalyzes the reaction between oxygen and glucose in order to generate an electrical signal. The catalyzed reaction produces gluconic acid and hydrogen peroxide. The hydrogen peroxide reacts electrochemically, and the oxidation of hydrogen peroxide at an electrode generates the current measured by the sensor. This process and glucose biosensors which incorporate it are well known in the art, including U.S. Pat. No. 7,226,978.

Generally, it is estimated that the ratio of concentration of glucose to oxygen in human tissues is about 100:1, or higher. The membranes described herein may be used to adjust this generally unfavorable concentration. The present selectively permeable membranes may alter the glucose concentration so that it is less than the concentration of oxygen at the enzyme layer. In certain embodiments, the membranes may be adjusted as described herein to increase the permeability of oxygen, while limited the permeability of glucose.

Generally, portions of this description are directed to various devices which measure the concentration of glucose within a biological fluid. However, the biosensors or membranes described herein are not limited to use in devices that measure the presence or concentration of glucose. The biosensors or membranes may be used in a variety of devices which detect the presence of other analytes.

In this disclosure, the term "analyte" is used according to its ordinary and customary definition as understood by a person of ordinary skill in the art. The term is not to be limited to a special or customized meaning, and refers without limitation to a substance or chemical constituent in a biological fluid that can be analyzed, such as blood, interstitial fluid, cerebral spinal fluid, lymph fluid, or urine. Analytes may include naturally occurring substances, artificial substances, metabolites, or reaction products. In some embodiments, the analyte for measurement by the sensing regions, devices, and methods may be glucose. However, other analytes are contemplated.

Other contemplated analytes include, but are not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-[beta] hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia hepatitis B virus, HCMV, HiV-1, HTLV-1, Leber hereditary optic neuropathy, MCAD, RNA, PKU, *Plasmodium vivax*, sexual differentiation, 21-deoxy-cortisol); desbutylhalofantrine; dihydropteridine reductase; diptheria/tetanus antitoxin; erythrocyte arginase; erythrocyte protoporphyrin; esterase D; fatty acids/acylglycines; free [beta]-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, [beta]); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococus granulosus*, *Entamobea histolytica*, enterovirus. *Giardia duodenalisa*, *Helicobacter pylori*, hepatitis B virus, herpes virus, HIV-1. IgE (atopic disease), influenza virus, *Leishmania donovani*, *leptospira*, measles/mumps/rubella, *Mycobacterium leprae*, *Mycoplasma pneumoniae*, *Myoglobin*, *Onchocerca volvulus*, parainfluenza virus, *Plasmodiumrn falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins, and hormones naturally occurring in blood or interstitial fluids may also constitute analytes in certain embodiments. The analyte may be naturally present in the biological fluid or endogenous, for example, a metabolic product, a hormone, an antigen, an antibody, and the like. Alternatively, the analyte may be introduced into the body or exogenous, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrate, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin), narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy), anabolic steroids; and nicotine.

Furthermore, the metabolic products of drugs and pharmaceutical compositions are also considered analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

In certain preferred embodiments, the biosensors or selectively permeable membranes described herein may be incorporated into the implantable sensors described in U.S. Pat. No. 6,551,838; U.S. Pat. No. 7,648,677; U.S. Pat. No. 7,510,551 and U.S. Pat. No. 7,604,628, which are assigned to MicroCHIPS, Inc., as well as the sensors described in U.S. Patent Application Publications No. 2008/0302659; No. 2008/0033260; and No. 2005/0096587, all of which are expressly incorporated herein by reference.

The biosensors or membranes described herein also may be incorporated or used in a variety of glucose-measuring devices in the prior art, such as U.S. Pat. No. 6,001,067 to Shults et al.; U.S. Pat. No. 6,702,857 to Brauker et al., U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kumrik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. 5,985,129 to Cough et al.; PCT Patent Application Publication No. WO 04/021877 to Caduff; U.S. Pat. No. 5,494,562 to Maley et al.; U.S. Pat. No. 6,120,676 to Heller et al., and U.S. Pat. No. 6,542,765 to Guy et al. Generally, it is understood that the biosensors or membranes described herein are applicable to a variety of glucose measuring devices.

Figure 2:
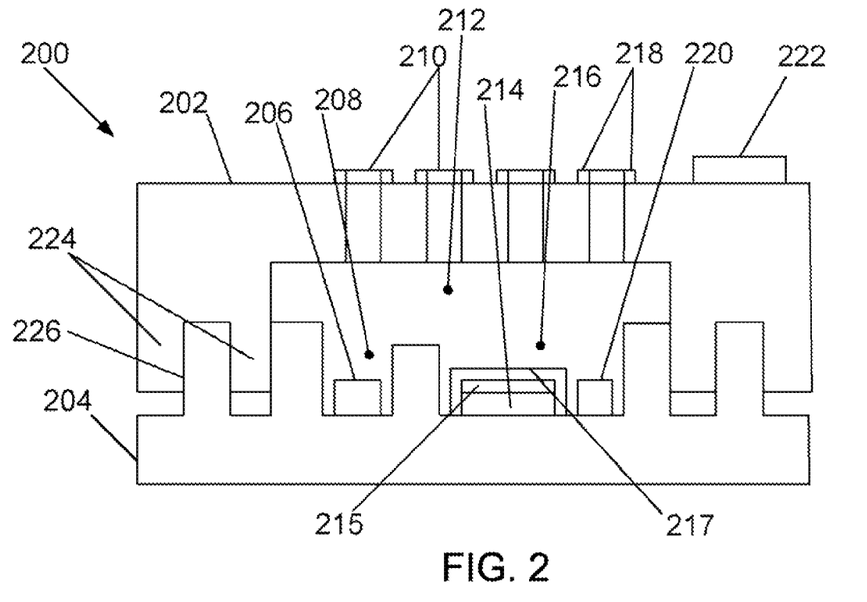
FIG. 2 is a cross-sectional view illustrating a sensor device in which electrode components of the sensor device are provided in separate, discrete reservoirs or wells.
Figure 3:
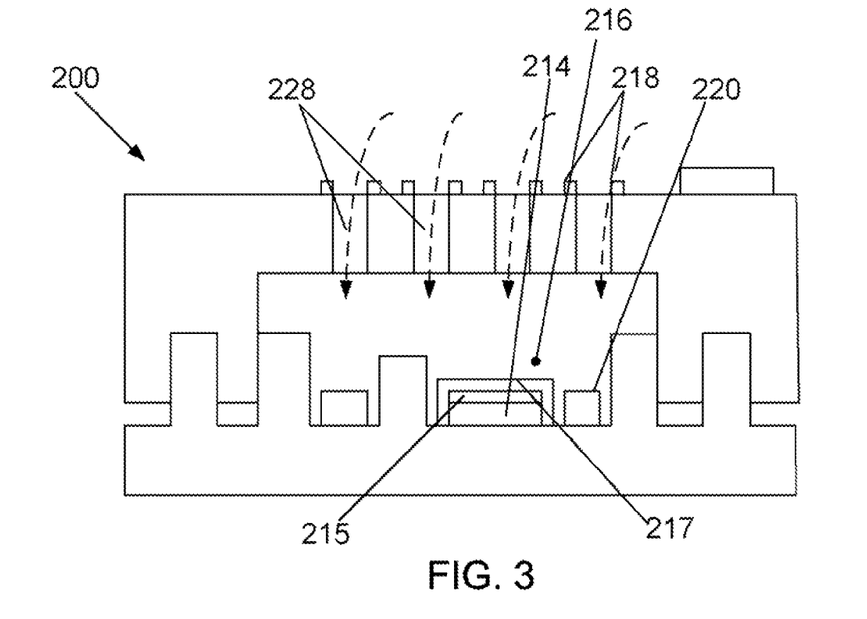
FIG. 3 is a cross-sectional view illustrating a sensor device with open reservoir caps.

FIGS. 2 and 3 illustrate an embodiment of a sensor device in which electrode components of the sensor device are provided in separate, discrete reservoirs or wells. In the illustrated embodiment, the discrete reservoirs are fluidly connected such that the fluid entering the device through the reservoir openings, e.g., after rupturing or displacing the reservoir cap, may be exposed to the reference electrode and working electrode simultaneously. FIGS. 2 and 3 show an embodiment of a sensor device 200 comprising two substrate portions 202 and 204. The substrate portion 202 includes joint portions 224 which engage a joint portion 226 of the substrate portion 204 to form a hermetically sealed reservoir 212. An example of the upper substrate portion 202a is described in U.S. Pat. No. 7,604,628, which is incorporated herein by reference. The two substrate portions 202 and 204 may be attached together, for example, by a compression cold weld. Alternatively or additionally, an adhesive may be used to bond substrate portions 202 and 204 together.

The substrate portion 202 comprises a plurality of reservoir caps 210, which hermetically seal the reservoir 212 and its contents from the environment around the device 220. One or more leads 218 are electrically connected to each of the reservoir caps 210. In the illustrated embodiment, two leads 218 are electrically connected to each reservoir cap 210 to allow for selective rupturing of the reservoir caps 210 by electrothermal ablation.

The reservoir 212 comprises two, discrete sub-reservoirs, or wells, 208 and 216. The reservoir 208 contains a reference electrode 206 and the reservoir 216 contains a working electrode 214 and an auxiliary electrode 220. At least a portion of the working electrode 214 is covered by an enzyme 215 such as glucose oxidase. The enzyme 215 is covered with a selectively permeable membrane 217, which may be one of the polymer mixtures described herein. A counter electrode 222 is provided on an exterior surface of the device 200.

The sensor device 200 also includes power and control systems (not shown) that power and control disintegration of the one or more reservoir caps 210 and operatively connected to the electrodes 214, 206, 220, and 222. The control system may open the reservoir caps 340 at a selected time, as illustrated in FIG. 3, for example by transmitting an electric current suitable for electrothermally ablating the reservoir caps 210, thereby exposing openings 228 in the substrate 202 and allowing a fluid (e.g., an interstitial fluid or other bodily fluid) to enter the reservoir 212. The analyte of interest in the fluid then can be detected by the working electrode 214.

Although a single reservoir is shown in several of the embodiments described above and illustrated in the appended drawings, it is understood that the sensor device may include an array of multiple reservoirs, such as, two, four, ten, twenty, or one hundred reservoirs, each reservoir being associated with a discrete or shared combination of electrodes to form a sensor. Likewise, other combinations of substrate structures, reservoir shapes/sidewall angles, reservoir cap disintegration means, and the like, besides the particular combinations illustrated and described herein, are contemplated.

The present invention may be further understood with reference to the following non-limiting examples.

Example 1

Preparation of Polymer Mixture Solution

To a 20 mL glass vial, 0.6∊0.03 g of 2% TECOPHILIC™ SP-85A-150 solution in THF was added dropwise with a 5 mL pipette. Similarly, 4.00±0.05 g of a 2% BIOSPAN®-S solution in THF was added. Thereafter, 2.00±0.04 g of a 2% PURSIL® AL solution in THF was added to the vial. Before sealing the vial with a PTFE cap, a stir bar was added to the contents. The vial was then placed on a magnetic stir plate, and the contents of the vial were stirred for at least 5 minutes to form a homogeneous solution. Unused portions of the solution were stored at room temperature.

Example 2

Deposition of the Enzyme Layer

The deposition of the enzyme layer occurred in a cleanroom with a relative humidity of <50% and a temperature of 22° C.±3° C. The enzyme solution was removed from the freezer, and left at room temperature to thaw. A 5% glutaraldehyde solution was prepared by pipetting 4.0±0.2 mL of HPLC grade water into a clear 19×65 mm glass vial. With a pipette, 1.0±0.01 mL of 25% glutaraldehyde was added to the water in the vial. The solution was mixed thoroughly by repeatedly aspirating and dispensing the solution with a 200-microliter pipettor.

A fan and humidifier were then placed in a BIODOT® (BioDot, Inc. Irvine, Calif., U.S.A.) chamber. Multiple substrates or plates were then mounted on a fixture within the chamber. The fixture was then placed on the BIODOT® platform. The computer program SCIENION SCIFLEXARRAYER™ by BIODOT® was then launched. The program was then used to ready the nozzle for delivery of the enzyme solution. Using a 20-microliter pipettor, 10 μL of the 5% glutaraldehyde solution were added to the thawed enzyme vial. The contents were mixed thoroughly by gently aspirating and dispensing the solution with a pipettor. 400 μL of the enzyme solution was then pipetted into the well of the well plates that had been previously chosen to be used by the computer program. Upon activation, the machine dispensed the enzyme solution. After deposition of the enzyme solution, the crosslinker chamber was started.

Example 3

Deposition of Polymer Mixture Solution

The deposition of the polymer mixture solution was performed in a cleanroom with a temperature of 22° C.±3° C. A 2 mL glass vial was filled with 2 mL of THF, and capped. To a 10 μL. Hamilton syringe equipped with a 32-gauge needle was added 10 μL of the polymer mixture solution. The Hamilton syringe was then mounted on a filling station. To the filling station's stage, a fixture containing sensor chips was secured. A computer program was then engaged to conduct the deposition. Before the deposition, the syringe was primed by dipping the needle in the 2 mL vial of THF for approximately 10 seconds. The needle was then wiped clean with a cleanroom wiper. The polymer mixture solution was then dispensed from the needle several times to bring it to the tip of the needle. Dispensing of the solution was then initiated.

The resulting membranes were visually inspected for defects with a microscope. The membranes were typically stored in a glove box under a reduced atmosphere of nitrogen gas.

Example 4

Deposition of Polymer Solution Mixture

A polymer solution mixture containing 75% by volume of a 6% TECOFLEX™ SG 85A solution in THF; 15% by volume of a 6% poly(ethylene glycol) bis(3-aminopropyl) terminated solution in THF; and 10% by volume of a 6% silicone adhesive RTV solution in THF is prepared as described herein. After thorough mixing, 0.4-0.6 μL of the polymer solution mixture was delivered to a cavity on a rectangular shaped substrate. The cavity was approximately 1 mm×1.2 mm. The solvent was allowed to evaporate at ambient temperature and pressure to form a film. The solvent evaporated in less than 5 minutes.

A solvent mixture of water and THF (1:2) was then prepared, and 0.8 μL of the solvent mixture were deposited on the film to partially dissolve the film and reform the film's surface. After the solvent mixture evaporated, the cavity containing the restructured film was placed in a chamber, which was equilibrated with the vapor of glutaraldehyde at 37° C. The glutaraldehyde cross-linked the polymer components of the membrane. The restructuring of the film's surface with the solvent mixture was then repeated to maintain consistency of the sensor's sensitivity. The sensor was kept at room temperature and at a relative humidity of >20% for 12 hours to allow the residual silicone to cure.

All documents cited in the Detailed Description are, in relevant part, incorporated herein by reference the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Modifications and variations of the methods and devices described herein will be obvious to those skilled in the art from the foregoing detailed description. Such modifications and variations are intended to come within the scope of the appended claims.

I claim:

1. A selectively permeable membrane for a biosensor, comprising:
 a solvent cast film which comprises a mixture of
  a first polyether-based thermoplastic polyurethane copolymer, and
  a polyether-based polyurethane copolymer,
 wherein the polyether-based thermoplastic polyurethane copolymer, or the polyether-based polyurethane copolymer, or both comprise at least one siloxane repeat unit.

2. The membrane of claim 1, wherein when the polyether-based polyurethane copolymer comprises at least one siloxane repeat unit, the copolymers are present in the film in a proportion in the range of about 1:3 to about 1:4 polyether-based thermoplastic polyurethane copolymer to polyether-based polyurethane copolymer.

3. The membrane of claim 1, wherein the solvent cast film further comprises a second polyether-based thermoplastic polyurethane copolymer.

4. The membrane of claim 3, wherein the second polyether-based thermoplastic polyurethane copolymer comprises at least one siloxane repeat unit.

5. The membrane of claim 3, wherein when the first polyether-based thermoplastic polyurethane copolymer comprises at least one siloxane repeat unit, the copolymers are present in the film in a proportion in the range of about 2:1:1 polyether-based polyurethane copolymer to first polyether-based thermoplastic polyurethane copolymer to second polyether-based thermoplastic polyurethane copolymer.

6. The membrane of claim 1, wherein the first polyether-based thermoplastic polyurethane copolymer is TECOPHILIC™ SP-85A-150 (aliphatic hydrophilic polyether-based thermoplastic polyurethane copolymer).

7. The membrane of claim 1, wherein the first polyether-based thermoplastic polyurethane copolymer is PURSIL® silicone polyether-based thermoplastic polyurethane copolymer.

8. The membrane of claim 1, wherein the at least one siloxane repeat unit comprises a silicone repeat unit.

9. The membrane of claim 1, wherein the polyether-based polyurethane copolymer comprises BIOSPAN® (polyether-based polyurethane copolymer) or BIOSPAN®-S (polyether-based polyurethane copolymer containing silicone).

10. A selectively permeable membrane for a biosensor, comprising:
 a solvent cast film which consists essentially of a mixture of
  a polyether-based thermoplastic polyurethane copolymer, and
  a polyether-based polyurethane copolymer,
 wherein the polyether-based thermoplastic polyurethane copolymer, or the polyether-based polyurethane copolymer, or both comprise at least one siloxane repeat unit.

11. The membrane of claim 10, wherein when the polyether-based polyurethane copolymer comprises at least one siloxane repeat unit, the copolymers are present in the film in a proportion in the range of about 1:3 to about 1:4 thermoplastic polyurethane copolymer to polyether-based polyurethane copolymer.

12. A selectively permeable membrane for a biosensor, comprising:
 a solvent cast film which consists essentially of a mixture of
  a first polyether-based thermoplastic polyurethane copolymer,
  a polyether-based polyurethane copolymer, and
  a second polyether-based thermoplastic polyurethane copolymer that is different from the first polyether-based thermoplastic polyurethane copolymer,
 wherein at least one of the first polyether-based thermoplastic polyurethane copolymer, the polyether-based polyurethane copolymer, and the second polyether-based thermoplastic polyurethane copolymer comprises at least one siloxane repeat unit.

13. The membrane of claim 12, wherein the second polyether-based thermoplastic polyurethane copolymer comprises at least one siloxane repeat unit.

14. The membrane of claim 12, wherein when the first thermoplastic polyurethane copolymer comprises at least one siloxane repeat unit, the copolymers are present in the film in a proportion in the range of about 2:1:1 polyether-based polyurethane copolymer to first polyether-based thermoplastic polyurethane copolymer to second polyether-based thermoplastic polyurethane copolymer.

* * * * *